(12) United States Patent
Hershberger

(10) Patent No.: US 7,833,228 B1
(45) Date of Patent: Nov. 16, 2010

(54) METHOD AND INSTRUMENTATION FOR PERFORMING MINIMALLY INVASIVE HIP ARTHROPLASTY

(75) Inventor: Troy W. Hershberger, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 901 days.

(21) Appl. No.: 10/912,644

(22) Filed: Aug. 5, 2004

Related U.S. Application Data

(60) Provisional application No. 60/534,270, filed on Jan. 5, 2004.

(51) Int. Cl.
*A61B 17/00* (2006.01)

(52) U.S. Cl. .............................. 606/80; 606/84; 606/85; 606/86 R

(58) Field of Classification Search ............ 606/79–85, 606/86 R; 623/22.11, 22.12, 22.42, 23.15, 623/23.29; 407/12, 13, 29.14
See application file for complete search history.

(56) References Cited

U.S. PATENT DOCUMENTS

| | | | |
|---|---|---|---|
| 105,044 A | 7/1870 | Clark | |
| 152,776 A | 7/1874 | Stockwell | |
| 991,566 A | 5/1911 | Vernaz | |
| 1,178,310 A | 4/1916 | Getaz | |
| 4,306,550 A | 12/1981 | Forte | |
| 4,466,429 A | 8/1984 | Loscher et al. | |
| 4,473,070 A | 9/1984 | Matthews et al. | |
| 4,549,319 A | 10/1985 | Meyer | |
| 4,601,289 A | 7/1986 | Chiarizzio et al. | |
| 4,706,659 A | 11/1987 | Matthews et al. | |
| 4,739,750 A | * 4/1988 | Masse et al. | ................... 606/85 |
| 4,765,328 A | 8/1988 | Keller et al. | |
| 4,846,839 A | 7/1989 | Noiles | |
| 4,878,917 A | 11/1989 | Kranz et al. | |
| 4,921,493 A | 5/1990 | Webb, Jr. et al. | |

(Continued)

FOREIGN PATENT DOCUMENTS

DE 03801678 C1 8/1989

(Continued)

OTHER PUBLICATIONS

Berger, "Total Hip Arthroplasty Using the Minimally Invasive Two-Incision Approach," *Clinical Orthopaedics and Related Research*, vol. 417, 2003, pp. 232-241.

(Continued)

*Primary Examiner*—Eduardo C Robert
*Assistant Examiner*—Ellen C Hammond
(74) *Attorney, Agent, or Firm*—William F. Bahret

(57) ABSTRACT

A broach instrument for preparing the proximal medullary canal of a femur for receiving a hip stem implant includes lateral and medial broach segments that may be assembled and disassembled along a longitudinal plane of separation defined by longitudinal sliding surfaces. A respective longitudinal shaft is connected to a proximal end of each broach segment. Each longitudinal shaft has a respective impact head connected to a respective proximal end. The broach segments and/or shafts positively engage one another to resist lateral separation of the broach segments. Each broach segment may be inserted separately and sequentially through a minimal posterior incision and through the gluteus maximus and then be assembled within the patient for broaching.

30 Claims, 3 Drawing Sheets

U.S. PATENT DOCUMENTS

| | | | |
|---|---|---|---|
| 4,938,773 A | | 7/1990 | Strand |
| 5,006,121 A | | 4/1991 | Hafeli |
| 5,089,003 A | | 2/1992 | Fallin et al. |
| 5,108,437 A | | 4/1992 | Kenna |
| 5,169,402 A | * | 12/1992 | Elloy ........................ 606/85 |
| 5,171,277 A | * | 12/1992 | Roger ...................... 606/86 R |
| 5,190,550 A | | 3/1993 | Miller et al. |
| 5,203,595 A | | 4/1993 | Borzone et al. |
| 5,342,366 A | | 8/1994 | Whiteside et al. |
| 5,441,501 A | | 8/1995 | Kenyon |
| 5,443,471 A | | 8/1995 | Swajger |
| 5,507,830 A | | 4/1996 | DeMane et al. |
| 5,607,431 A | * | 3/1997 | Dudasik et al. .............. 606/80 |
| 5,653,712 A | * | 8/1997 | Stern ........................... 606/80 |
| 5,704,940 A | | 1/1998 | Garosi |
| 5,713,905 A | | 2/1998 | Goble et al. |
| 5,766,261 A | | 6/1998 | Neal et al. |
| 5,858,020 A | | 1/1999 | Johnson et al. |
| 6,090,146 A | | 7/2000 | Rozow, III et al. |
| 6,117,138 A | * | 9/2000 | Burrows et al. .............. 606/80 |
| 6,126,694 A | | 10/2000 | Gray, Jr. |
| 6,193,759 B1 | | 2/2001 | Ro et al. |
| 6,238,400 B1 | | 5/2001 | Bays |
| 6,238,436 B1 | | 5/2001 | Lob et al. |
| 6,428,578 B2 | | 8/2002 | White |
| 6,676,706 B1 | | 1/2004 | Mears et al. |
| 6,902,583 B2 | | 6/2005 | Gerbec et al. |
| 2002/0040244 A1 | | 4/2002 | Despres, III et al. |
| 2002/0058999 A1 | | 5/2002 | Dwyer et al. |
| 2002/0059000 A1 | | 5/2002 | Dwyer et al. |
| 2002/0099447 A1 | | 7/2002 | Mears et al. |
| 2002/0116067 A1 | | 8/2002 | Mears et al. |
| 2002/0151984 A1 | | 10/2002 | White |
| 2003/0130741 A1 | | 7/2003 | McMinn |
| 2003/0149487 A1 | | 8/2003 | Doubler et al. |

FOREIGN PATENT DOCUMENTS

| | | |
|---|---|---|
| DE | 04116507 C1 | 9/1992 |
| EP | 89810034 2 | 9/1989 |

OTHER PUBLICATIONS

Matta, "The Anterior Approach for Total Hip Replacement: Background and Operative Technique," HipandPelvis.com [on-line], © 2002-2003 [retrieved Dec. 31, 2003]. Retrieved from the Internet: http://www.hipandpelvis.com/physicians_corner/thr.htm. (2 pages).

Office Action, dated Apr. 1, 2009, in U.S. Appl. No. 11/030,019 (17 pages).

Office Action, dated Oct. 5, 2009, in U.S. Appl. No. 11/030,020 (11 pages).

Office Action, dated Apr. 15, 2010, in U.S. Appl. No. 11/030,020 (9 pages).

* cited by examiner

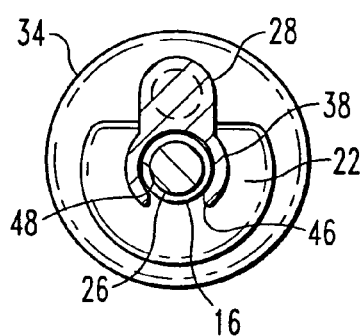
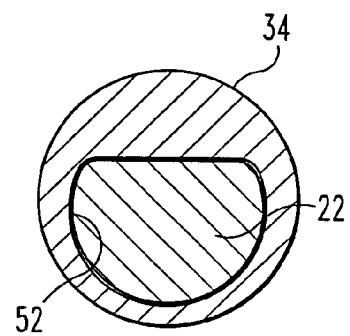
Fig. 4   Fig. 5
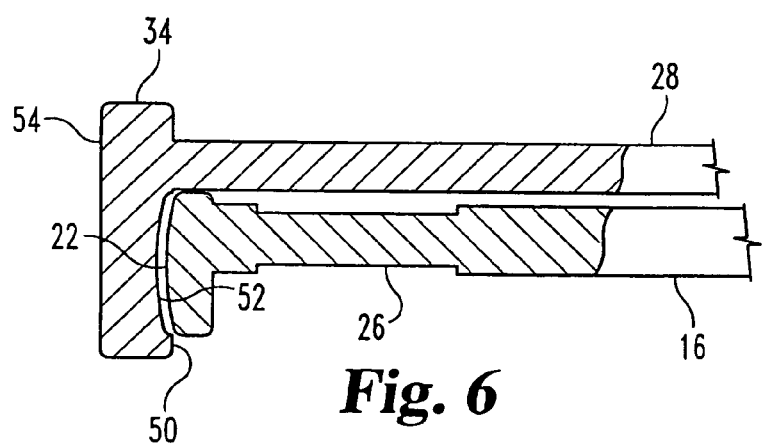
Fig. 6

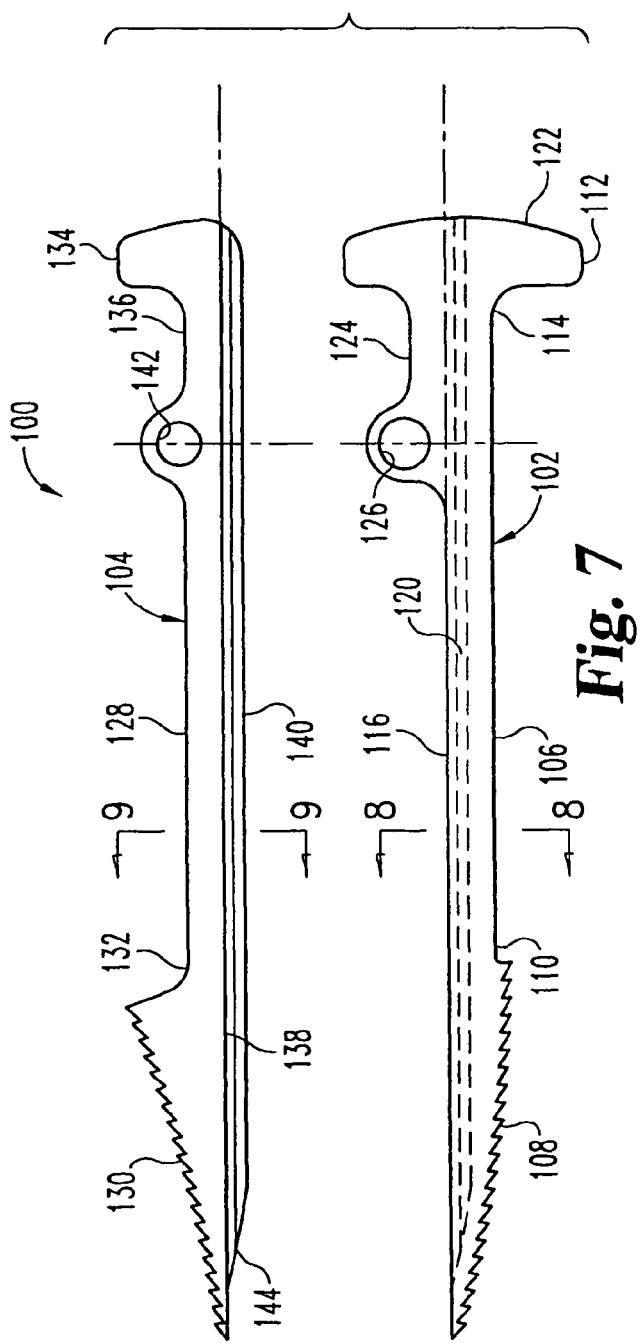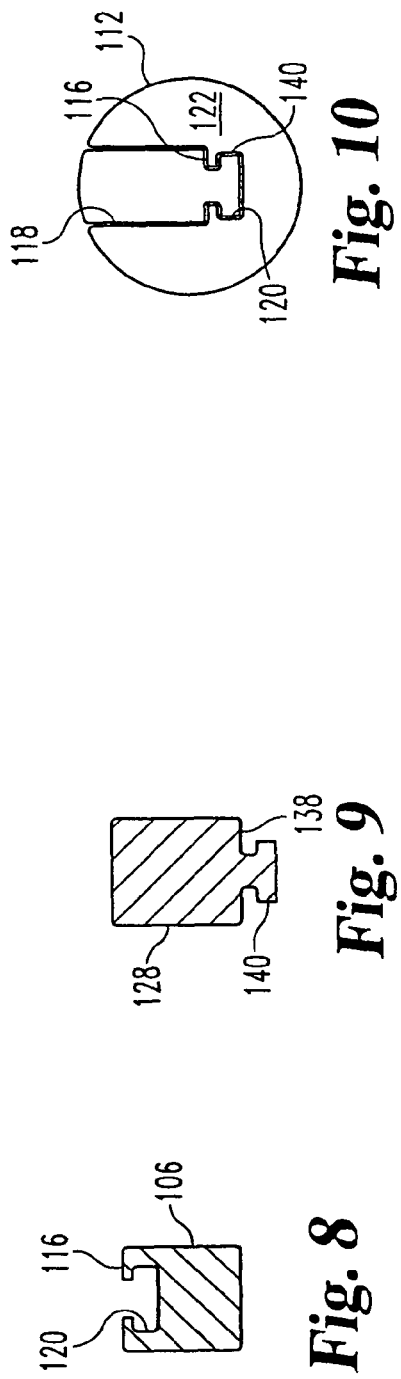

under the US 7,833,228 B1

METHOD AND INSTRUMENTATION FOR PERFORMING MINIMALLY INVASIVE HIP ARTHROPLASTY

CROSS-REFERENCE TO RELATED APPLICATIONS

This application claims the benefit of U.S. Provisional Patent Application No. 60/534,270, filed Jan. 5, 2004, which application is hereby incorporated by reference.

BACKGROUND OF THE INVENTION

This invention relates to methods and instruments for performing hip arthroplasty, and more particularly to broach instruments and methods for preparing the proximal femur to receive a femoral implant as part of an implantable hip prosthesis.

In one popular method of performing a total hip arthroplasty through two incisions, the femur is prepared by passing instrumentation through a small posterior lateral incision. This posterior incision is similar to the incision made when performing a conventional femoral intramedular nailing procedure except that the incision is located somewhat more superior. A second, direct lateral or anterior incision is made to facilitate the introduction of instrumentation for preparation of the acetabulum as well as to expose the femur from the anterior side. The surgeon is able to view the femur and resect the femoral head from this anterior side. Access along the femoral axis for reamers and broaches is most readily accomplished, however, through the posterior lateral incision. The surgeon bluntly divides the fibers of the gluteus maximus through the posterior incision to develop a small tunnel through which he may pass the femoral broaches, reamers and, eventually, the femoral implant. The femur is broached through the posterior lateral incision while the femur is viewed through the anterior incision.

There are disadvantages associated with the prior method and instrumentation described above. These include the necessity of making the posterior lateral incision large enough to accommodate passage of the full girth of the femoral broach and other instrumentation. Also, damage may be caused to the muscle fibers as well as the skin margins by excessive stretching of tissue and by repeatedly passing the broach and other instrumentation into and out of the posterior lateral incision.

SUMMARY OF THE INVENTION

One aspect of the present invention involves, in one embodiment, a broach instrument for preparing the proximal medullary canal of a femur for receiving a hip stem implant. The instrument includes a first broach segment having a first longitudinal surface and a second broach segment having a second longitudinal surface. The first and second broach segments have a first configuration in which the first and second broach segments are separated and a second configuration in which the second longitudinal surface slidably engages the first longitudinal surface.

Another aspect of the present invention involves a surgical method for preparing the proximal medullary canal of a femur of a patient for receiving a hip stem implant. A broach is provided that is divided longitudinally into at least two segments. Access to the proximal femur is provided through the gluteus maximus. One of the at least two broach segments is inserted through the gluteus maximus. Another broach segment is inserted through the gluteus maximus and the broach segments are interconnected together within the patient to form an assembled broach. The proximal medullary canal is broached with the assembled broach.

Other aspects and advantages of the present invention will be apparent from the following descriptions with reference to the drawings.

BRIEF DESCRIPTION OF THE DRAWINGS

FIG. 4 is a cross-section of the broach instrument taken along line 4-4 of FIG. 1 FIG. 5 is a cross-section of the broach instrument taken along line 5-5 of FIG. 1.

FIG. 6 is an enlarged view of the proximal end of the broach instrument of FIG. 1, shown in partial longitudinal section.

FIG. 7 is an exploded side view of another embodiment of a broach instrument according to the present invention.

FIG. 8 is a cross-section of the shaft of one component of the broach instrument taken along line 8-8 of FIG. 7.

FIG. 9 is a cross-section of the shaft of another component of the broach instrument taken along line 9-9 of FIG. 7.

FIG. 10 is an end view of the proximal end of the broach instrument of FIG. 7.

DETAILED DESCRIPTION OF THE PREFERRED EMBODIMENTS

Figure 1:
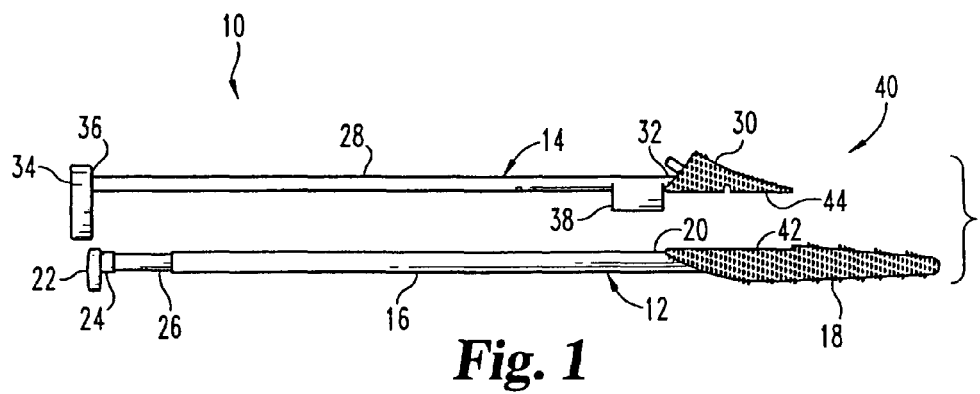
FIG. 1 is an exploded side view of one embodiment of a broach instrument according to the present invention.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device and such further applications of the principles of the invention as illustrated therein being contemplated as would normally occur to one skilled in the art to which the invention relates.

It is desired to reduce trauma to the patient during a total hip arthroplasty. One approach to reducing trauma is to provide a multi-piece broach. The multi-piece broach may include medial and lateral halves that may be inserted separately through a posterior lateral incision and assembled together intra-operatively prior to broaching. Because the broach is divided into separate pieces that are each of smaller girth than the assembled whole broach, the size of the incision necessary to accommodate passage of the separate broach pieces may be reduced. Furthermore, the surgeon may bluntly divide a smaller region of the fibers of the gluteus maximus to accommodate passage of the separate broach pieces. As a result, there is less stretching of and trauma to the gluteus maximus muscle and other nearby tissues than in prior procedures.

Referring to FIGS. 1-6, a first embodiment of a broach instrument 10 according to the present invention includes first and second halves 12 and 14. First half 12 includes a first shaft 16, a lateral broach segment 18 disposed at and connected to the distal end 20 of first shaft 16, and an impact head 22 disposed at and connected to the proximal end 24 of first shaft 16. First shaft 16 may be constructed integrally with lateral broach segment 18 or may be removably attached. Likewise, impact head 22 may be constructed integrally with first shaft 16 or may be removably attached, although it is preferred that shaft 16 and head 22 be integral. Near proximal end 24, first shaft 16 has a neck 26 of circular cross-section that is smaller in diameter than the remainder of shaft 16, which is otherwise substantially cylindrical. Alternatively, shaft 16 and neck 26 may have other cross-sectional geometries, and may be D-shaped, square or rectangular, for example. Second half 14 includes a second shaft 28, a medial broach segment 30 disposed at and connected to the distal end 32 of second shaft 28, and an impact head 34 disposed at and connected to the proximal end 36 of second shaft 28. Near distal end 32, a guide portion 38 extends laterally from second shaft 28 for slidably engaging and partially surrounding first shaft 16 to resist lateral separation of second half 14 from first half 12 when assembled thereto. Second shaft 28 as shown is cylindrical, but alternatively may have other cross-sectional geometries.

Figure 3:
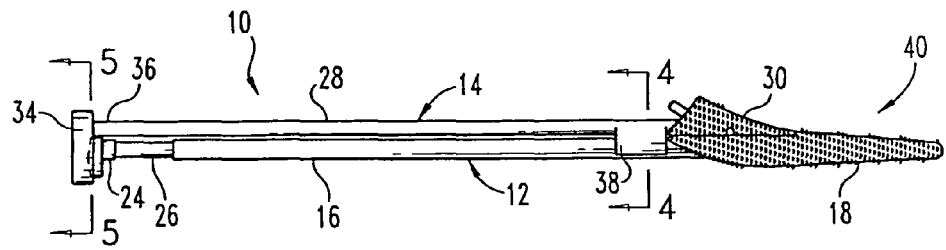
FIG. 3 is a side view of the fully assembled broach instrument of FIG. 1.

Medial broach segment 30 is configured to slidably engage lateral broach segment 18 to form a whole assembled broach 40, as best shown in FIG. 3. The assembled broach 40 may have an overall shape that is conventional and suitable for broaching the medullary canal of the proximal femur to prepare the femur to receive the stem portion of a femoral prosthesis as part of a total hip arthroplasty. The broach 40 is divided into segments 18 and 30 along a longitudinal plane of separation defined by medial planar surface 42 of lateral broach segment 18 and lateral planar surface 44 of medial broach segment 30. Medial planar surface 42 and lateral planar surface 44 slide longitudinally relative to one another.

Figure 2:
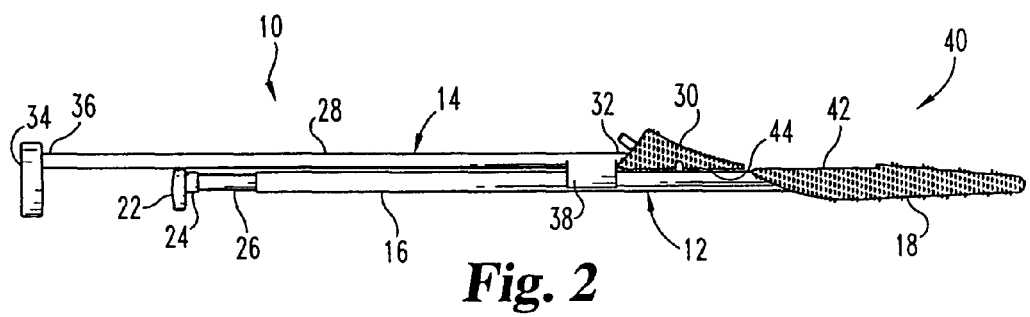
FIG. 2 is a side view of the partially assembled broach instrument of FIG. 1.

Referring to FIG. 2, broach instrument 10 is shown partially assembled. The instrument is assembled by first disposing second half 14 substantially parallel to first half 12 as generally shown in FIG. 1, but with distal end 32 of shaft 28 disposed proximate proximal end 24 of shaft 16. Next, guide portion 38 of second half 14 is laterally aligned with neck 26 of first half 12. Second half 14 is then moved laterally toward first half 12 until neck 26 is received within guide portion 38. Next, the surgeon may slide second half 14 longitudinally and distally relative to first half 12 with guide portion 38 partially enveloping and sliding along first shaft 16. When so disposed, lateral displacement of second half 14 relative to first half 12 is resisted, as described further below.

Referring now to FIG. 3, the surgeon continues to slide second half 14 in the distal direction until lateral planar surface 44 of medial broach segment 30 slides along medial planar surface 42 of lateral broach segment 18. The surgeon may slide second half 14 distally until lateral broach segment 18 and medial broach segment 30 are fully engaged, whereupon broach 40 assumes a conventional overall configuration.

With particular reference to FIG. 4, guide portion 38 has a longitudinal slot or gap 46 on the lateral side thereof that communicates with a substantially cylindrical longitudinal bore 48 defined within guide portion 38. Bore 48 has in internal diameter that is slightly greater than the major diameter of first shaft 16 such that guide portion 38 may be disposed in sliding relationship with first shaft 16. Slot or gap 46 has a width slightly greater than the diameter of neck 26 of first shaft 16. Neck 26 may be received through gap 46 when second half 14 is moved laterally toward first half 12 while guide portion 38 is aligned with the neck. Consequently, first and second halves 12 and 14 may be assembled together and slid longitudinally as described above and shown in FIGS. 2 and 3, and yet be restrained from lateral separation while in the assembled condition by virtue of the major diameter of first shaft 16 exceeding the width of slot or gap 46.

As shown in FIGS. 5 and 6, impact head 34 of second half 14 is substantially circular in transverse cross-section and is connected eccentrically to second shaft 28. The distal side 50 of impact head 34 includes a substantially D-shaped recess 52 for receiving impact head 22 of first half 12. Impact head 22 is substantially D-shaped in transverse cross-section and corresponds generally to the shape of recess 52, but is somewhat smaller in transverse dimensions to provide slight clearance when received within recess 52. As first and second halves 12 and 14 are assembled together and slid longitudinally as described above and shown in FIGS. 2 and 3, impact head 22 is received in nesting relationship within recess 52 of impact head 34 substantially simultaneously with medial planar surface 42 and lateral planar surface 44 of broach 40 becoming fully engaged. While so nested, impact heads 22 and 34 restrain first and second halves 12 and 14 from lateral separation. Consequently, when fully assembled as shown in FIG. 3, guide portion 38 restrains the distal portion of broach instrument 10 against lateral separation, whereas nested impact heads 22 and 34 restrain the proximal portion of broach instrument 10 against lateral separation.

The nested arrangement of impact heads 22 and 34 also provides for impact force applied to the proximal side 54 of impact head 34 to be transferred to impact head 22 and thus to shaft 16 of first half 12, and to be simultaneously transferred to shaft 28 of second half 14. Therefore, it is assured that first and second halves 12 and 14 move longitudinally in unison when so impacted, further assuring that medial broach segment 30 and lateral broach segment 18 likewise move longitudinally in unison.

In one preferred method of use, the broach instrument 10 may be used in a total hip arthroplasty procedure to prepare the proximal femur for receiving the femoral stem portion of an implantable hip prosthesis. An anterior incision is made to provide access to the acetabulum and femoral head. The femoral head is resected through the anterior incision in conventional fashion to expose the proximal femoral medullary canal. A posterior lateral incision is made in a location that provides access substantially along the femoral axis and the fibers of the gluteus maximus are bluntly divided.

Lateral broach segment 18 of first half 12 is introduced through the posterior incision and through the bluntly divided gluteus maximus and partly into the exposed medullary canal. Second half 14 is then assembled to first half 12 outside the incision as described above such that guide portion 38 is first aligned with reduced-diameter neck 26, then moved laterally such that neck 26 is received within bore 48 of guide portion 38, and then moved longitudinally and distally such that guide portion 38 engages first shaft 16. Second half 14 is slid further distally until medial broach segment 30 is introduced through the posterior incision and through the bluntly divided gluteus maximus, in which first half 12 continues to reside. Further distal sliding of second half 14 relative to first half 12 results in medial broach segment 30 being partially introduced into the femoral canal until fully assembled with lateral broach segment 18 such that broach 40 assumes its full configuration. Once so assembled, broach instrument 10 is used to broach the proximal femur in conventional fashion.

When broaching is completed, broach instrument 10 is removed and disassembled in reverse order. Second half 14 is first withdrawn through the posterior incision and disassembled from first half 12. Thereafter, first half 12 is withdrawn through the posterior lateral incision. By introducing and removing the broach instrument in separate portions through the posterior incision, where each portion has a girth less than the overall girth of the assembled broach, the size of the posterior lateral incision and the region of bluntly divided muscle fibers can be minimized, thereby minimizing tissue trauma.

Referring to FIGS. 7-10, another embodiment of a broach instrument 100 according to the present invention includes first and second halves 102 and 104. First half 102 includes a first shaft 106, a lateral broach segment 108 disposed at the distal end 110 of first shaft 106, and an impact head 112 disposed at the proximal end 114 of first shaft 106. Preferably, shaft 106, broach segment 108, and head 112 are integrally constructed. Shaft 106 is generally rectangular in cross-section. A medial longitudinal planar surface 116 runs the length of first half 102, including broach segment 108 and shaft 106, and forms the floor of a radial channel 118 that extends in the medial direction in impact head 112, as shown best in FIG. 10. A longitudinal, undercut T-shaped groove 120 is disposed in planar surface 116 and runs substantially the length of broach instrument 100, as shown best in FIGS. 8 and 10, and is open at the proximal surface 122 of impact head 112. Groove 120 functions similarly to guide portion 38 of the embodiment of broach instrument 10 of FIG. 1, described above, to prevent lateral separation of first and second halves 102, 104 when assembled. Alternatively, groove 120 may be an undercut, dove-tail shaped groove. The proximal portion of first shaft 106 includes a medially extending portion 124 having a transverse bore 126 therethrough which serves to lock first half 102 to second half 104, as described further below.

Second half 104 includes a second shaft 128, a medial broach segment 130 disposed at the distal end 132 of second shaft 128, and an impact head 134 disposed at the proximal end 136 of second shaft 128. Preferably, shaft 128, broach segment 130, and head 134 are integrally constructed. Shaft 128 is generally rectangular in cross-section. Head 134 extends in the medial direction and is generally rectangular in cross-section and sized to closely fit within channel 118 of first half 102, as shown in FIG. 10. A longitudinal planar surface 138 runs the length of second half 104, including broach segment 130, shaft 128, and head 134. A longitudinal, T-shaped spline 140 extends laterally from planar surface 138 and runs substantially the length of second half 104, as shown best in FIGS. 9 and 10, for cooperation with T-shaped groove 120 of first half 102. Alternatively, spline 140 may be dove-tail shaped if groove 120 is dove-tail shaped. Near proximal end 136, a transverse bore 142 extends through second shaft 128 for cooperation with bore 126 of first shaft 106.

Lateral broach segment 118 and medial broach segment 130 are configured to slidably engage one another to form a whole assembled broach that may have an overall shape that is conventional and suitable for broaching the medullary canal of the proximal femur. The broach is divided into segments 118 and 130 along a longitudinal plane of separation defined by medial planar surface 116 of lateral broach segment 118 and first shaft 106, and lateral planar surface 138 of medial broach segment 130 and second shaft 128. Medial planar surface 116 and lateral planar surface 138 slide longitudinally relative to one another. T-shaped spline 140 and T-shaped groove 120 likewise slide longitudinally relative to one another and positively engage to prevent lateral separation of first half 102 from second half 104 when assembled.

The broach instrument 100 may be assembled and used surgically similarly to the manner in which broach instrument 10 is assembled and used, as described above. Lateral broach segment 118 of first half 102 is introduced through the posterior incision and through the bluntly divided gluteus maximus and partly into the exposed medullary canal. Second half 104 is then assembled to first half 102 by first disposing second half 104 substantially parallel to first half 102 as generally shown in FIG. 7, but with the distal end 144 of spline 140 longitudinally aligned with the open proximal end of groove 120 at proximal surface 122 of head 112. Next, second half 104 is moved distally relative to first half 102 until spline 140 is received within groove 120. Second half 104 is moved longitudinally and distally until medial broach segment 130 is introduced through the posterior incision and through the bluntly divided gluteus maximus, in which first half 102 continues to reside. Next, the surgeon may continue to slide second half 104 distally relative to first half 102 to partially enter the femoral canal with the lateral planar surface 138 of medial broach segment 130 sliding along medial planar surface 116 of head 112 and shaft 106. The surgeon may slide second half 104 distally until lateral broach segment 118 and medial broach segment 130 become fully engaged, whereupon the broach assumes a conventional overall configuration. When fully engaged, bores 126 and 142 are aligned and a pin (not shown) may be inserted therethrough to lock first half 102 and second half 104 together so that they may be moved longitudinally as a unit. Once locked, broach instrument 100 may be used to broach the proximal femur in conventional fashion. When broaching is completed, broach instrument 100 is disassembled and removed in reverse order.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A broach instrument for preparing the proximal medullary canal of a femur for receiving a hip stem implant, said proximal medullary canal having an axis, said broach instrument comprising:

a first serrated broach segment having a first longitudinal surface defining a first longitudinal axis;

a second serrated broach segment having a second longitudinal surface;

a first, elongate longitudinal shaft disposed at a proximal end of said first broach segment and extending proximally therefrom; and a second, elongate longitudinal shaft disposed at a proximal end of said second broach segment and extending proximally therefrom;

wherein said longitudinal shafts are both longer than both of said broach segments;

wherein said first and second broach segments have a first configuration in which they are separated and a second configuration in which said second longitudinal surface longitudinally slidably engages said first longitudinal surface along said first longitudinal axis, which in normal use of said broach instrument is substantially parallel to said medullary canal axis, said broach segments having a fully engaged state in which they are side by side with maximum longitudinal overlap of their serrations; and wherein said shafts are designed and arranged to inhibit separate delivery of impact force to said first and second broach segments when they are fully engaged, whereby said segments move as a unit during broaching of said proximal medullary canal.

2. The broach instrument of claim 1, further comprising means for connecting said first and second shafts in longitudinal sliding engagement.

3. The broach instrument of claim 2, wherein said connecting means resists lateral separation of said first and second broach segments.

4. The broach instrument of claim 1, further comprising:

wherein said longitudinal shafts are substantially straight.

5. The broach instrument of claim 4, wherein said first and second longitudinal shafts have respective proximal end members with which said shafts cooperatively inhibit separate delivery of impact force to said first and second broach segments when said broach segments are fully engaged.

6. The broach instrument of claim 5, wherein said respective proximal end members of said shafts comprise first and second impact heads which are nested, when said broach segments are fully engaged, such that an impact applied to one of said impact heads is transferred to the other of said impact heads.

7. The broach instrument of claim 6, wherein said first and second impact heads, when nested, resist lateral separation of said first and second longitudinal shafts.

8. The broach instrument of claim 7,
wherein said instrument is configured such that said first and second longitudinal shafts are parallel to each other in said second configuration of said broach segments.

9. The broach instrument of claim 8, further comprising a guide portion connected to one of said longitudinal shafts and receiving the other of said longitudinal shafts in sliding engagement.

10. The broach instrument of claim 9, wherein said guide portion is configured to resist lateral separation of said first and second longitudinal shafts.

11. The broach instrument of claim 10, wherein the other of said longitudinal shafts includes a neck of reduced cross-section and said guide portion includes a gap of sufficient width to receive said neck laterally therethrough.

12. The broach instrument of claim 4, further comprising a guide portion connected to one of said longitudinal shafts and receiving the other of said longitudinal shafts in sliding engagement.

13. The broach instrument of claim 12, wherein said guide portion is configured to resist lateral separation of said first and second longitudinal shafts.

14. The broach instrument of claim 13, wherein the other of said longitudinal shafts includes a neck of reduced cross-section and said guide portion includes a gap of sufficient width to receive said neck laterally therethrough.

15. The broach instrument of claim 8, wherein said longitudinal shafts are parallel to said first longitudinal axis defined by said first broach segment.

16. The broach instrument of claim 4, wherein said longitudinal shafts are substantially parallel to said first longitudinal axis defined by said first broach segment.

17. A broach instrument for preparing the proximal medullary canal of a femur for receiving a hip stem implant, comprising:
a serrated broach separated longitudinally into a first elongate broach segment and second elongate broach segment with respective facing surfaces and with respective serrated outer surfaces radially opposed to said facing surfaces; and
means for interconnecting said first and second broach segments by longitudinal displacement of said first broach segment relative to said second broach segment to form a whole broach having said first and second broach segments fully engaged, said interconnecting means including a first elongate shaft extending proximally from a proximal end of said first broach segment, and a second elongate shaft extending proximally from a proximal end of said second broach segment;
wherein said whole broach has a longitudinal axis extending through the distal tip thereof and said facing surfaces of said broach segments are substantially parallel to said longitudinal axis and transversely fixed with respect to each other after formation of said whole broach; and
wherein said shafts are designed and arranged to inhibit relative displacement of said first and second broach segments in response to force applied to either one in the distal direction along said longitudinal axis while said segments are fully engaged within said proximal medullary canal, whereby said segments move as a unit during broaching of said proximal medullary canal.

18. The broach instrument of claim 17, wherein said interconnecting means resists lateral separation of said first and second broach segments, and wherein said broach segments are mutually engaged along a substantial portion of each of their lengths when interconnected to form said whole broach.

19. The broach instrument of claim 18, wherein said interconnecting means includes a guide portion connected to one of said longitudinal shafts.

20. The broach instrument of claim 18, wherein said longitudinal shafts are substantially straight shafts.

21. The broach instrument of claim 20, wherein said elongate shafts are substantially parallel to said longitudinal axis of said whole broach.

22. A broach instrument for preparing the proximal medullary canal of a femur for receiving a hip stem implant, said proximal medullary canal having an axis, said broach instrument comprising:
a first serrated broach segment having a first longitudinal surface;
a separable second serrated broach segment having a second longitudinal surface;
a first, elongate longitudinal shaft disposed at a proximal end of said first broach segment and extending proximally therefrom; and
a second, elongate longitudinal shaft disposed at a proximal end of said second broach segment and extending proximally therefrom;
wherein said longitudinal shafts are both longer than both of said broach segments;
wherein said broach instrument has an assembled configuration in which said first broach segment is laterally adjacent said second broach segment and substantially fixed laterally with respect thereto, and said first and second longitudinal surfaces thereof are substantially parallel to said medullary canal axis in normal use of said broach instrument, said broach segments having a fully engaged state with maximum longitudinal overlap; and
wherein said shafts are designed and arranged to inhibit separate delivery of impact force to said first and second broach segments when they are fully engaged, whereby said segments move as a unit during broaching of said proximal medullary canal.

23. The broach instrument of claim 22, further comprising means for connecting said first and second shafts in longitudinal sliding engagement.

24. The broach instrument of claim 23, wherein said connecting means resists lateral separation of said first and second broach segments.

25. The broach instrument of claim 24, wherein said first and second longitudinal shafts have respective proximal end members with which said shafts cooperatively inhibit separate delivery of impact force to said first and second broach segments when said broach segments are fully engaged.

26. The broach instrument of claim 25, wherein said respective proximal end members of said shafts comprise first and second impact heads which are nested, when said broach segments are fully engaged, such that an impact applied to one of said impact heads is transferred to the other of said impact heads.

27. The broach instrument of claim 26, wherein said first and second impact heads, when nested, resist lateral separation of said first and second longitudinal shafts.

28. The broach instrument of claim 27, wherein said connecting means includes a guide portion connected to one of said longitudinal shafts and receiving the other of said longitudinal shafts in sliding engagement.

29. The broach instrument of claim 28, wherein the other of said longitudinal shafts includes a neck of reduced cross-section and said guide portion includes a gap of sufficient width to receive said neck laterally therethrough, and wherein at least one of said shafts is straight.

30. The broach instrument of claim 29, wherein said longitudinal shafts are substantially parallel to said medullary canal axis in normal use of said broach instrument.

\* \* \* \* \*